United States Patent [19]

Hermeling

[11] Patent Number: 5,243,066
[45] Date of Patent: Sep. 7, 1993

[54] ALKYL 2-ARYL-2,2-DIALKOXYACETATES, THE PREPARATION THEREOF AND A METHOD OF USING THEM FOR PREPARING ARYLGLYOXYLIC ESTERS

[75] Inventor: Dieter Hermeling, Frankenthal, Fed. Rep. of Germany

[73] Assignee: BASF Aktiengesellschaft, Ludwigshafen, Fed. Rep. of Germany

[21] Appl. No.: 907,974

[22] Filed: Jul. 2, 1992

[30] Foreign Application Priority Data

Jul. 5, 1991 [DE] Fed. Rep. of Germany ....... 4122315

[51] Int. Cl.$^5$ .............................................. C07C 69/76
[52] U.S. Cl. .................................................... 560/60
[58] Field of Search ........................................... 560/60

[56] References Cited

FOREIGN PATENT DOCUMENTS 1286037 1/1969 Fed. Rep. of Germany.

OTHER PUBLICATIONS

Tetrahedron Letters, vol. 21, pp. 4997–5000 (by John M. Domagala), "A mild, rapid, and convenient esterfication of α-keto acids".

Liebigs Ann. Chem. 1980, 1271–1282, "Oxidation von 1,3–diphenyl-1,3–propandionen mit Thallium (III)–nitrat in Methanol".

Synthesis, 1983, pp. 203–205, "A Simple Procedure for the Acetalization of Carbonyl Compounds" by Chan, Brook & Chaly.

Primary Examiner—Paul J. Killos
Attorney, Agent, or Firm—Keil & Weinkauf

[57] ABSTRACT

Alkyl 2-aryl-2,2-dialkoxyacetates are prepared by electrochemical oxidation of alkyl 2-arylacetates and are used to prepare arylglyoxylic esters.

3 Claims, No Drawings

ALKYL 2-ARYL-2,2-DIALKOXYACETATES, THE PREPARATION THEREOF AND A METHOD OF USING THEM FOR PREPARING ARYLGLYOXYLIC ESTERS

The present invention relates to alkyl 2-aryl-2,2-dialkoxyacetates, to a process for the preparation thereof by electrochemical oxidation and the use thereof for preparing arylglyoxylic esters.

Dialkyl acetals of arylglyoxylic esters can be prepared, for example by the method of Synthesis (1983), 203-205, by reacting arylglyoxylic esters with methanol in the presence of chlorotrimethylsilane or, by the method of Tetrahedron Lett. 21 (1980) 4997, by a combined acid-catalyzed acetalization/esterification of arylglyoxylic acids.

Since, however, it is not the acetals but the arylglyoxylic esters themselves which are the more interesting compounds, and the described acetalizations start from the arylglyoxylic acids or esters, these synthesis have no economic importance.

Methyl 2,2-dimethoxy-2-(4-methoxyphenyl)acetate is a breakdown product in the oxidation of a 1,3-diphenyl-1,3-propanedione with thallium(III) nitrate (Liebigs Ann. Chem. (1980) 1271-1282). However, this reaction has no economic importance because of the specific oxidizing agent.

The acetals are, however, when they can be synthesized straightforwardly, important precursors for arylglyoxylic esters because, on the one hand, they protect the keto group from unwanted reaction but, at the same time, permit reactions on the ester group and because, on the other hand, they can be converted very easily and in virtually quantitative yield to the corresponding arylglyoxylic esters. The arylglyoxylic esters have a wide range of possible uses and serve, for example, according to EP 242 081 as precursors for herbicides, fungicides and insecticides, according to EP 25 271 as precursors for antibiotics or according to JP 61 097 247 as precursors for α-amino acids.

It is an object of the present invention to make alkyl arylglyoxylic dialkyl acetals obtainable in a straightforward manner.

We have found that this object is achieved by the straightforward preparation of alkyl 2-aryl-2,2-dialkoxyacetates of the formula I

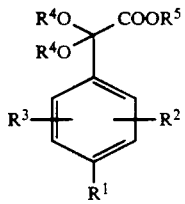

where $R^1$ is straight-chain or branched $C_1$-$C_{12}$-alkyl, $C_3$-$C_{12}$-cycloalkyl, $C_4$-$C_{12}$-alkyl-cycloalkyl, $C_1$-$C_{12}$-alkoxy or $C_6$-$C_{14}$-aryloxy; $R^2$ and $R^3$ are, independently of one another, hydrogen, halogen or straight-chain or branched $C_1$-$C_{12}$-alkyl, $C_1$-$C_{12}$-alkoxy, $C_3$-$C_{12}$-cycloalkyl, $C_4$-$C_{12}$-alkylcycloalkyl, $C_6$-$C_{14}$-aryloxy or $C_6$-$C_{14}$-aryl; $R^4$ is $C_1$-$C_6$-alkyl, and $R^5$ is straight-chain or branched $C_1$-$C_{20}$-alkyl, by oxidizing alkyl arylacetates of the formula II

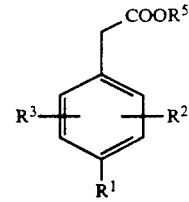

where $R^1$, $R^2$, $R^3$ and $R^5$ have the abovementioned meanings, electrochemically in the presence of an alcohol $R^4OH$, where $R^4$ is $C_1$-$C_6$-alkyl.

The alkyl 2-aryl-2,2-dialkoxyacetates of the formula I prepared in this way are novel, although $R^1$ cannot be methoxy when $R^2$ and $R^3$ are hydrogen and $R^4$ and $R^5$ are methyl.

Suitable groups for the substituents $R^1$ to $R^5$ are the following:

$R^1$ straight-chain or branched $C_1$-$C_{12}$-alkyl, preferably $C_1$-$C_8$-alkyl such as methyl, ethyl, n-propyl, isopropyl, n-butyl, isobutyl, sec-butyl, tert-butyl, n-pentyl, tert-amyl, 1,1-dimethylbutyl, 1,1-dimethylpentyl, 1,1-dimethylhexyl, 1,1,2,2-tetramethylpropyl, particularly preferably tert-butyl, tert-amyl and 1,1,2,2-tetramethylpropyl, straight-chain or branched $C_1$-$C_{12}$-alkoxy, preferably $C_1$-$C_8$-alkoxy such as methoxy, ethoxy, propyloxy, n-butyloxy, isobutyloxy, sec-butyloxy, tert-butyloxy, n-pentyloxy, tert-amyloxy, n-hexyloxy, n-heptyloxy, n-octyloxy, particularly preferably methoxy, ethoxy, tert-butyloxy and n-hexyloxy, cycloalkyl of 3 to 12 carbons, preferably cyclopentyl, cyclohexyl, cycloheptyl, or alkyl-cycloalkyl of 4 to 12 carbons, such as 1-methylcyclopentyl, 1-methylcyclohexyl, 1-ethylcyclohexyl, 1,4-dimethylcyclohexyl, 1,3-dimethylcyclohexyl, 1,3,5-trimethylcyclohexyl, 1-isopropylcyclohexyl, 1-tert-butylcyclohexyl, particularly preferably 1-methylcyclopentyl, 1-methylcyclohexyl and 1,3,5-trimethylcyclohexyl, $C_6$-$C_{14}$-aryloxy such as phenoxy, 1-naphthyloxy, 2-naphthyloxy, particularly preferably phenoxy, $R^2$ and $R^3$ independently of one another hydrogen, straight-chain or branched $C_1$-$C_{12}$-alkyl, preferably $C_1$-$C_8$-alkyl such as methyl, ethyl, n-propyl, isopropyl, n-butyl, isobutyl, sec-butyl, tert-butyl, n-pentyl, tert-amyl, 1,1-dimethylbutyl, 1,1-dimethylpentyl, 1,1-dimethylhexyl, 1,1,2,2-tetramethylpropyl, particularly preferably tert-butyl, tert-amyl and 1,1,2,2-tetramethylpropyl, straight-chain or branched $C_1$-$C_{12}$-alkoxy, preferably $C_1$-$C_8$-alkoxy such as methoxy, ethoxy, propyloxy, n-butyloxy, isobutyloxy, sec-butyloxy, tert-butyloxy, n-pentyloxy, tert-amyloxy, n-hexyloxy, n-heptyloxy, n-octyloxy, particularly preferably methoxy, ethoxy, tert-butyloxy and n-hexyloxy, $C_3$-$C_{12}$-cycloalkyl, preferably $C_3$-$C_7$-cycloalkyl such as cyclopropyl, cyclobutyl, cyclopentyl, cyclohexyl, cycloheptyl, particularly preferably cyclopentyl and cyclohexyl, alkyl-cycloalkyl of 4 to 12 carbons, such as 1-methylcyclopentyl, 1-methylcyclohexyl, 1-ethylcyclohexyl, 1,4-dimethylcyclohexyl, 1,3-dimethylcyclohexyl, 1,3,5-trimethylcyclohexyl, 1-isopropylcyclohexyl, 1-tert-butylcyclohexyl, particularly preferably 1-methylcyclopentyl, 1-methylcyclohexyl and 1,3,5-trimethylcyclohexyl, $C_6$-$C_{14}$-aryloxy such as phenoxy, 1-naphthyloxy, 2-naphthyloxy, particularly preferably phenoxy, $C_6$-$C_{14}$-aryl such as phenyl, 1-naphthyl, 2-naphthyl, preferably phenyl, halogen such as fluorine, chlorine, bromine, preferably fluorine and chlorine, $R^4$ straight-chain $C_1$-$C_6$-alkyl, preferably $C_1$-$C_4$-alkyl such as methyl, ethyl, propyl, butyl, particularly preferably methyl and ethyl, $R^5$ straight-chain or branched $C_1$-$C_{20}$-alkyl, preferably $C_1$-$C_{12}$-alkyl such as methyl, ethyl, n-propyl, isopropyl, n-butyl, isobutyl, sec-butyl, tert-butyl, n-pentyl, tert-amyl, n-hexyl, n-heptyl, n-octyl, n-nonyl, n-decyl, n-undecyl, n-dodecyl, particularly preferably methyl, ethyl, isopropyl and tert-butyl.

Any desired combination of the substituents is possible for the claimed process, but it is preferable that the α atoms on the substituents $R^1$, $R^2$ and $R^3$ do not carry hydrogen because the yields of the electrochemical oxidation decrease because of by-products which arise owing to hydrogens on the α-C atoms.

Preferred compounds are:
ethyl 2,2-dimethoxy-2-(4-methoxyphenyl)acetate
tert-butyl 2,2-dimethoxy-2-(4-methoxyphenyl)acetate
methyl 2,2-diethoxy-2-(4-methoxyphenyl)acetate
tert-butyl 2,2-diethoxy-2-(4-methoxyphenyl)acetate
methyl 2,2-dimethoxy-2-(4-ethoxyphenyl)acetate
ethyl 2,2-dimethoxy-2-(4-ethoxyphenyl)acetate
tert-butyl 2,2-dimethoxy-2-(4-ethoxyphenyl)acetate
methyl 2,2-diethoxy-2-(4-ethoxyphenyl)acetate
ethyl 2,2-diethoxy-2-(4-ethoxyphenyl)acetate
tert-butyl 2,2-diethoxy-2-(4-ethoxyphenyl)acetate
methyl 2,2-dimethoxy-2-(4-hexyloxyphenyl)acetate
tert-butyl 2,2-dimethoxy-2-(4-hexyloxyphenyl)acetate
ethyl 2,2-dimethoxy-2-(4-hexyloxyphenyl)acetate
methyl 2,2-diethoxy-2-(4-hexyloxyphenyl)acetate
ethyl 2,2-diethoxy-2-(4-hexyloxyphenyl)acetate
tert-butyl 2,2-diethoxy-2-(4-hexyloxyphenyl)acetate
methyl 2,2-dimethoxy-2-(4-tert-butyloxyphenyl)acetate
ethyl 2,2-dimethoxy-2-(4-tert-butyloxyphenyl)acetate
tert-butyl 2,2-dimethoxy-2-(4-tert-butyloxyphenyl)acetate
methyl 2,2-diethoxy-2-(4-tert-butyloxyphenyl)acetate
ethyl 2,2-diethoxy-2-(4-tert-butyloxyphenyl)acetate
tert-butyl 2,2-diethoxy-2-(4-tert-butyloxyphenyl)acetate
methyl 2,2-dimethoxy-2-(4-phenoxyphenyl)acetate
tert-butyl 2,2-dimethoxy-2-(4-phenoxyphenyl)acetate
ethyl 2,2-dimethoxy-2-(4-phenoxyphenyl)acetate
methyl 2,2-diethoxy-2-(4-phenoxyphenyl)acetate
ethyl 2,2-diethoxy-2-(4-phenoxyphenyl)acetate
tert-butyl 2,2-diethoxy-2-(4-phenoxyphenyl)acetate
methyl 2,2-dimethoxy-2-(3,4-dimethoxyphenyl)acetate
ethyl 2,2-dimethoxy-2-(3,4-dimethoxyphenyl)acetate
tert-butyl 2,2-dimethoxy-2-(3,4-dimethoxyphenyl)acetate
methyl 2,2-diethoxy-2-(3,4-dimethoxyphenyl)acetate
ethyl 2,2-diethoxy-2-(3,4-dimethoxyphenyl)acetate
tert-butyl 2,2-diethoxy-2-(3,4-dimethoxyphenyl)acetate
methyl 2,2-dimethoxy-2-(4-tert-butylphenyl)acetate
ethyl 2,2-dimethoxy-2-(4-tert-butylphenyl)acetate
tert-butyl 2,2-dimethoxy-2-(4-tert-butylphenyl)acetate
methyl 2,2-diethoxy-2-(4-tert-butylphenyl)acetate
ethyl 2,2-diethoxy-2-(4-tert-butylphenyl)acetate
tert-butyl 2,2-diethoxy-2-(4-tert-butylphenyl)acetate The electrochemical oxidations can be carried out in electrolysis cells conventional in industry. Undivided continuous flow cells are preferably used. Examples of suitable anodes are noble metal electrodes such as platinum or oxide electrodes such as Ti/RuO$_x$, RuO$_2$ or Cr$_2$O$_3$. Graphite is the preferred anode material. Examples of suitable cathodes are steel, iron, copper, nickel, zinc and carbon as well as noble metals such as platinum. Graphite is the preferred cathode material. The electrolyte is composed of the starting compound of the formula II, of the alcohol $R^4OH$ and of an auxiliary electrolyte. Suitable auxiliary electrolytes are neutral salts, acids and bases. Examples of neutral salts are fluorides such as KF, sulfonates such as NaSO$_3$Ph, sulfates such as (CH$_3$)$_4$NSO$_4$CH$_3$, tetrafluoroborates such as NaBF$_4$, phosphates and phosphonates. Examples of acids are sulfuric acid, alkyl- and arylsulfonic acids such as methyl- or benzenesulfonic acid. Examples of bases which are used are alcoholates such as NaOCH$_3$ or hydroxides such as KOH.

The electrolyte has the following composition, for example:

1 to 49, preferably 5 to 3%, by weight of alkyl arylacetate of the formula II,
0.1 to 5, preferably 0.2 to 3%, by weight of auxiliary electrolyte
50 to 98.9, preferably 70 to 95%, by weight of alcohol $R^4OH$ The current density can be chosen within wide limits for the process according to the invention, for example from 0.1 to 25 A/dm$^2$, preferably from 1 to 10 A/dm$^2$. The temperatures can also be varied within wide limits. Thus, the oxidations can be carried out at from 0° to 120° C., preferably at from 20° to 80° C. The electrolysis temperature depends on, inter alia, the alcohol $R^4OH$. The temperature in the process are always below the boiling point of the alcohol $R^4OH$. The electrolyses are preferably carried out under atmospheric pressure, but can also be carried out under superatmospheric pressure. The resulting elevation in boiling point means that it is also possible, for example, to electrolyze in methanol above 60° C.

Some of the alkyl 2-arylacetates of the formula II can be bought, or they can be prepared in a conventional manner from the correspondingly substituted acetic acids.

Very subtantial conversion of the alkyl 2-arylacetates of the formula II is possible. The electrolyses can be carried out both continuously and batchwise. Intermediates (ethers) and unreacted percursors can be returned to the reaction. The electrolysis discharge is worked up by conventional methods, preferably by distillation.

The arylglyoxylic esters can be prepared from the resulting alkyl 2-aryl-2,2-dialkoxyacetates by hydrolysis in a conventional manner (see, for example, Houben-Weyl, Methoden der organischen Chemie, 4th Edition, GeorgThieme-Verlag, Stuttgart, 1954, Oxygen Compounds II, 7/1, Aldehydes, pages 423-428).

EXAMPLES

Example 1

Electrosynthesis of methyl 2,2-dimethoxy-2-(4-methoxyphenyl)acetate
Apparatus: undivided cell with 11 bipolar electrodes
Anodes: graphite
Electrolyte: 300 g (1.667 mol) of methyl 2-(4-methoxyphenyl)acetate, 30 g of sodium benzenesulfonate and 2670 g of methanol
Cathodes: graphite
Electrolysis temperature: 40° C.
Electrolysis with 5.6 F/mol of methyl 2-(4-methoxyphenyl)acetate.
The electrolyte is pumped at 200 l/h through the cell during the electrolysis.

Working up

After the electrolysis is complete, the methanol is removed by distillation under atmospheric pressure, the conducting salt is removed by filtration and the filtrate is purified by distillation under reduced pressure. 9.8 g (47 mmol; 3%) of methyl 2-methoxy-2-(4-methoxyphenyl)acetate and 240.2 g (1.001 mol; 60%) of methyl 2,2-dimethoxy-2-(4-methoxyphenyl)acetate are obtained. The methyl 2-methoxy-2-(4-methoxyphenyl)acetate is returned as intermediate to the reaction. The selectivity calculated from this is 62%. Boiling point 123° C./8 mbar

Example 2

Electrosynthesis of methyl 2,2-dimethoxy-2-(3,4-dimethoxyphenyl)acetate

Methyl 2-(3,4-dimethoxyphenyl)acetate is electrolyzed, and working up is carried out, as described in Example 1.

Electrolyte: 300 g (1.429 mol) of methyl 2-(3,4-dimethoxyphenyl)acetate, 30 g of sodium benzenesulfonate and 2670 g of methanol Electrolysis temperature: 52° C.

Electrolysis with 6 F/mol of methyl 2-(3,4-dimethoxyphenyl)acetate

The electrolyte is pumped at 200 l/h through the cell during the electrolysis.

Working up and purification by distillation under reduced pressure result in 280.6 g (1.039 mol; 73%) of methyl 2,2-dimethoxy-2(3,4-dimethoxyphenyl)acetate. Boiling point 153° C./1 mbar

Example 3

Electrosynthesis of ethyl 2,2-diethoxy-2-(4-n-hexyloxyphenyl)acetate

Ethyl 2-(4-n-hexyloxyphenyl)acetate is electrolyzed, and working up is carried out, as described in Example 1.

Number of bipolar electrodes: 9

Electrolyte: 93.8 g (355 mmol) of ethyl 2-(4-n-hexyloxyphenyl)acetate, 2.1 g of sodium benzenesulfonate and 529 g of ethanol Electrolysis temperature: 50° C.

Electrolysis with 8 F/mol of ethyl 2-(4-n-hexyloxyphenyl)acetate.

The electrolyte is pumped at 20 l/h through the cell during the electrolysis.

Working up and purification by distillation under reduced pressure result in 6.6 g (21 mmol; 6%) of ethyl 2-ethoxy-2-(4-n-hexyloxyphenyl)acetate (which is returned to the reaction) and 66.2 g (188 mmol; 53%) of ethyl 2,2-diethoxy-2-(4-n-hexyloxyphenyl)acetate. The selectivity calculated from this is 56%. Boiling point 168° C./1 mbar.

Example 4

Electrosynthesis of ethyl 2,2-diethoxy-2-(4-methoxyphenyl)acetate

Ethyl 2-(4-methoxyphenyl)acetate is electrolyzed, and working up is carried out, as described in Example 1.

Number of bipolar electrodes: 9

Electrolyte: 93.8 g (484 mmol) of ethyl 2-(4-methoxyphenyl)acetate, 2 g of sodium benzenesulfonate and 525 g of ethanol Electrolysis temperature: 48° C.

Electrolysis with 7 F/mol of ethyl 2-(4-methoxyphenyl)acetate.

The electrolyte is pumped at 20 l/h through the cell during the electrolysis.

Working up and purification by distillation under reduced pressure result in 7.6 g (32 mmol; 7%) of ethyl 2-ethoxy-2-(4-methoxyphenyl)acetate (which is returned to the reaction) and 86.8 g (308 mmol; 64%) of ethyl 2,2-diethoxy-2-(4-methoxyphenyl)acetate. The selectivity calculated from this is 69%.

Boiling point 143° C./3 mbar.

Example 5

Electrosynthesis of ethyl 2,2-diethoxy-2-(4-methoxyphenyl)acetate

Ethyl 2-(4-methoxyphenyl)acetate is electrolyzed, and working up is carried out, as described in Example 1.

Number of bipolar electrodes: 9

Electrolyte: 93.8 g (484 mmol) of ethyl 2-(4-methoxyphenyl)acetate, 6.2 g of sodium benzenesulfonate and 525 g of ethanol Electrolysis temperature: 14° C.

Electrolysis with 6 F/mol of ethyl 2-(4-methoxyphenyl)acetate.

The electrolyte is pumped at 20 l/h through the cell during the electrolysis.

Working up and purification by distillation under reduced pressure result in 7.9 g (35 mmol; 7%) of ethyl 2-methoxy-2-(4-methoxyphenyl)acetate (which is returned to the reaction) and 74.5 g (293 mmol; 61%) of ethyl 2,2-dimethoxy-2-(4-methoxyphenyl)acetate. The selectivity calculated from this is 66%.

Boiling point 131° C./3 mbar.

Example 6

Electrosynthesis of methyl 2,2-dimethoxy-2-(4-tert-butylphenyl)acetate

Methyl 2-(4-tert-butylyphenyl)acetate is electrolyzed, and working up is carried out, as described in Example 1.

Number of bipolar electrodes: 9

Electrolyte: 93.8 g (455 mmol) of methyl 2-(4-tert-butylphenyl)acetate, 6.2 g of sodium benzenesulfonate and 525 g of ethanol Electrolysis temperature: 48° C.

Electrolysis with 34 F/mol of methyl 2-(4-tert-butylyphenyl)acetate

The electrolyte is pumped at 20 l/h through the cell during the electrolysis.

Working up and purification by distillation under reduced pressure result in 6.0 g (25 mmol; 6%) of methyl 2-methoxy-2-(4-tert-butylphenyl)acetate (which is returned to the reaction) and 45.8 g (172 mmol; 38%) of methyl 2,2-dimethoxy-2-(4-tert-butylphenyl)acetate. The selectivity calculated from this is 40%.

Boiling point 142° C./3 mbar.

We claim:

1. An alkyl 2-aryl-2,2-dialkoxyacetate of the formula I

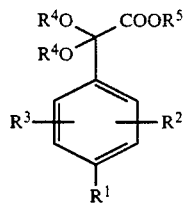

where

R[1] is straight-chain or branched $C_1-C_{12}$-alkyl, $C_3-C_{12}$-cycloalkyl, $C_4-C_{12}$-alkyl-cycloalkyl, $C_1-C_{12}$-alkoxy or $C_6-C_{14}$-aryloxy;

R[2] and R[3] are, independently of one another, hydrogen, halogen or straight-chain or branched $C_1-C_{12}$-alkyl, $C_1-C_{12}$-alkoxy, $C_3-C_{12}$-cycloalkyl, $C_4-C_{12}$-alkyl-cycloalkyl, $C_6-C_{14}$-aryloxy or $C_6-C_{14}$-aryl;

R[4] is $C_1-C_6$-alkyl, and

R[5] is straight-chain or branched $C_1-C_{20}$-alkyl, with the proviso that R[1] cannot be methoxy when R[2] and R[3] are hydrogen and R[4] and R[5] are methyl.

2. An alkyl 2-aryl-2,2-dialkoxyacetate as defined in claim 1, where the alkyl radical R[1] and the alkyl and cycloalkyl radicals R[2] and R[3] are $C_4-C_{12}$ radicals without a hydrogen on the α-C atom.

3. An alkyl 2-aryl-2,2-dialkoxyacetate as defined in claim 1, where R[1] is $C_1-C_6$-alkoxy and/or R[4] and R[5] are, independently of one another, methyl or ethyl.

* * * * *